(12) United States Patent
Vanderpool et al.

(10) Patent No.: US 12,354,279 B2
(45) Date of Patent: Jul. 8, 2025

(54) MOVEMENT TRACKING

(71) Applicant: Zimmer US, Inc., Warsaw, IN (US)

(72) Inventors: Matthew Vanderpool, Warsaw, IN (US); John Lally, Portland, OR (US); Ruvim Micsanschi, Vancouver, WA (US); Eric Cook, Warsaw, IN (US)

(73) Assignee: Zimmer US, Inc., Warsaw, IN (US)

( * ) Notice: Subject to any disclaimer, the term of this patent is extended or adjusted under 35 U.S.C. 154(b) by 463 days.

(21) Appl. No.: 17/830,043

(22) Filed: Jun. 1, 2022

(65) Prior Publication Data

US 2022/0392082 A1 Dec. 8, 2022

Related U.S. Application Data

(60) Provisional application No. 63/195,878, filed on Jun. 2, 2021.

(51) Int. Cl.
*G06T 7/20* (2017.01)
*A61B 5/00* (2006.01)
(Continued)

(52) U.S. Cl.
CPC .............. *G06T 7/20* (2013.01); *A61B 5/0077* (2013.01); *A61B 5/1072* (2013.01);
(Continued)

(58) Field of Classification Search
CPC ........... G06T 7/20; G06T 7/0014; G06T 7/60; G06T 2200/24; G06T 2207/10016;
(Continued)

(56) References Cited

U.S. PATENT DOCUMENTS

| | | |
|---|---|---|
| 7,981,057 B2 | 7/2011 | Stewart |
| 9,693,284 B2 | 6/2017 | Abedi |
| (Continued) | | |

FOREIGN PATENT DOCUMENTS

| | | |
|---|---|---|
| CN | 117916812 A | 4/2024 |
| JP | 2024526774 A | 7/2024 |
| (Continued) | | |

OTHER PUBLICATIONS

"U.S. Appl. No. 16/851,606, Response filed Nov. 21, 2022 to Restriction Requirement mailed Sep. 27, 2022", 7 pgs.
(Continued)

*Primary Examiner* — Ayodeji O Ayotunde
(74) *Attorney, Agent, or Firm* — SCHWEGMAN LUNDBERG & WOESSNER, P.A.

(57) ABSTRACT

Systems and methods may be used for evaluating a patient after completion of an orthopedic surgery on a portion of a body part of the patient. In an example, the method includes capturing, using a camera of the device, a series of images of the patient in motion, determining respective lengths of the body part in each of the series of images based on comparing the body part in each of the series of images to a skeletal model, and identifying a maximum length of the body part from the respective lengths. The method may include displaying an indication corresponding to the maximum length.

20 Claims, 8 Drawing Sheets

(51) Int. Cl.
| | |
|---|---|
| *A61B 5/107* | (2006.01) |
| *G06T 7/00* | (2017.01) |
| *G06T 7/60* | (2017.01) |
| *G16H 30/40* | (2018.01) |
| *H04N 5/265* | (2006.01) |
| *H04N 23/60* | (2023.01) |

(52) U.S. Cl.
CPC .......... *A61B 5/1079* (2013.01); *G06T 7/0014* (2013.01); *G06T 7/60* (2013.01); *G16H 30/40* (2018.01); *H04N 5/265* (2013.01); *H04N 23/64* (2023.01); *A61B 2505/05* (2013.01); *G06T 2200/24* (2013.01); *G06T 2207/10016* (2013.01); *G06T 2207/30008* (2013.01); *G06T 2207/30196* (2013.01)

(58) Field of Classification Search
CPC . G06T 2207/30008; G06T 2207/30196; A61B 5/1072
See application file for complete search history.

(56) References Cited

U.S. PATENT DOCUMENTS

| | | | |
|---|---|---|---|
| 9,782,122 | B1 | 10/2017 | Pulliam et al. |
| 9,795,299 | B2 | 10/2017 | Russell |
| 9,895,105 | B2 | 2/2018 | Romem |
| 9,936,877 | B2 | 4/2018 | Kotz et al. |
| 10,076,286 | B1 | 9/2018 | Bajaj et al. |
| 10,216,904 | B2 | 2/2019 | Hughes et al. |
| 10,535,244 | B2 | 1/2020 | Treacy et al. |
| 10,561,360 | B2 | 2/2020 | Amiot et al. |
| 10,912,480 | B2 | 2/2021 | Sridhar et al. |
| 2004/0021660 | A1 | 2/2004 | Ng-Thow-Hing et al. |
| 2007/0103471 | A1 | 5/2007 | Yang et al. |
| 2013/0095459 | A1 | 4/2013 | Tran |
| 2015/0320343 | A1 | 11/2015 | Utsunomiya et al. |
| 2015/0325270 | A1 | 11/2015 | Utsunomiya et al. |
| 2016/0151013 | A1 | 6/2016 | Atallah et al. |
| 2016/0227483 | A1 | 8/2016 | Wang et al. |
| 2016/0278868 | A1* | 9/2016 | Berend ................ A61B 5/1127 |
| 2016/0302721 | A1 | 10/2016 | Wiedenhoefer et al. |
| 2017/0344919 | A1 | 11/2017 | Chang et al. |
| 2019/0272917 | A1 | 9/2019 | Couture et al. |
| 2019/0283247 | A1 | 9/2019 | Chang et al. |
| 2020/0335222 | A1* | 10/2020 | Winterbach ............ A61B 5/112 |
| 2020/0352441 | A1 | 11/2020 | Soykan et al. |
| 2020/0383112 | A1 | 12/2020 | Soro et al. |
| 2021/0065870 | A1 | 3/2021 | Spooner et al. |
| 2021/0282652 | A1 | 9/2021 | Donnelly et al. |
| 2023/0114876 | A1 | 4/2023 | Brincat et al. |
| 2024/0212866 | A1 | 6/2024 | Winterbach et al. |
| 2024/0312630 | A1 | 9/2024 | Van Andel et al. |

FOREIGN PATENT DOCUMENTS

| | | |
|---|---|---|
| WO | WO-2020123935 A1 | 6/2020 |
| WO | WO-2020123954 A1 | 6/2020 |
| WO | WO-2020247890 A1 | 12/2020 |
| WO | WO-2023288060 A1 | 1/2023 |

OTHER PUBLICATIONS

"U.S. Appl. No. 16/851,606, Restriction Requirement mailed Sep. 27, 2022", 6 pgs.
"International Application Serial No. PCT/US2022/037284, Invitation to Pay Additional Fees mailed Oct. 11, 2022", 17 pgs.
Andreu-Perez, Javier, et al., "From Wearable Sensors to Smart Implants—Toward Pervasive and Personalized Healthcare", IEEE Transactions on Biomedical Engineering, IEEE, USA, vol. 62, No. 12, (Dec. 1, 2015), 2750-2762.
Misic, D, et al., "Real-Time Monitoring of Bone Fracture Recovery by Using Aware, Sensing, Smart, and Active Orthopedic Devices", IEEE Internet of Things Journal, IEEE, USA, vol. 5, No. 6, (Dec. 1, 2018), 4466-4473.
"U.S. Appl. No. 16/851,606, Non Final Office Action mailed Mar. 9, 2023", 12 pgs.
"European Application Serial No. 22185079.5, Extended European Search Report mailed Apr. 6, 2023", 13 pgs.
"International Application Serial No. PCT/US2022/037284, International Search Report mailed Dec. 2, 2022", 8 pgs.
"International Application Serial No. PCT/US2022/037284, Written Opinion mailed Dec. 2, 2022", 15 pgs.
"U.S. Appl. No. 16/851,606, Advisory Action mailed Aug. 10, 2023", 4 pgs.
"U.S. Appl. No. 16/851,606, Final Office Action mailed Jun. 14, 2023", 15 pgs.
"U.S. Appl. No. 16/851,606, Final Office Action mailed Dec. 13, 2023", 15 pgs.
"U.S. Appl. No. 16/851,606, Non Final Office Action mailed Sep. 22, 2023", 13 pgs.
"U.S. Appl. No. 16/851,606, Response filed May 31, 2023 to Non Final Office Action mailed Mar. 9, 2023", 11 pgs.
"U.S. Appl. No. 16/851,606, Response filed Jul. 28, 2023 to Final Office Action mailed Jun. 14, 2023", 9 pgs.
"U.S. Appl. No. 16/851,606, Response filed Dec. 1, 2023 to Non Final Office Action mailed Sep. 22, 2023", 8 pgs.
"U.S. Appl. No. 16/851,606, Supplemental Amendment filed Jun. 6, 2023", 11 pgs.
"U.S. Appl. No. 18/576,700, Preliminary Amendment Filed Jan. 4, 2024", 8 pgs.
"U.S. Appl. No. 18/603,842, Non Final Office Action mailed Sep. 29, 2024", 18 pgs.
"U.S. Appl. No. 18/603,842, Response filed Dec. 12, 2024 to Non Final Office Action mailed Sep. 29, 2024", 8 pgs.
"Australian Application Serial No. 2022311928, First Examination Report mailed Oct. 15, 2024", 4 pgs.
"European Application Serial No. 22185079.5, Response filed Nov. 10, 2023 to Extended European Search Report mailed Apr. 6, 2023", 20 pgs.
"European Application Serial No. 22754226.3, Response Filed Aug. 22, 2024 to Communication pursuant to Rules 161(1) and 162 EPC", 9 pgs.
"International Application Serial No. PCT/US2022/037284, International Preliminary Report on Patentability mailed Jan. 25, 2024", 17 pgs.
Ferrari, A., et al., "Gait analysis contribution to problems identification and surgical planning in CP patients: an agreement study", Eur J Phys Rehabil Med 51.1, (2015), 39-48.
Van Egmond, Nienke, et al., "Gait analysis before and after corrective osteotomy in patients with knee osteoarthritis and a valgus deformity", Knee surgery, sports traumatology, arthroscopy 25, (2017), 2904-2913.

* cited by examiner

MOVEMENT TRACKING

CLAIM OF PRIORITY

This application claims the benefit of priority to U.S. Provisional Application No. 63/195,878 filed Jun. 2, 2021, titled "MOVEMENT TRACKING," which is hereby incorporated herein by reference in its entirety.

BACKGROUND

Orthopedic patient care may require surgical intervention, such as for upper extremities (e.g., a shoulder or elbow), knee, hip, etc. For example, when pain becomes unbearable for a patient, surgery may be recommended. Postoperative care may include immobility of a joint ranging from weeks to months, physical therapy, or occupational therapy. Immobilization within the upper extremity may lead to long term issues, such as "Frozen shoulder" where a shoulder capsule thickens and becomes stiff and tight. Physical therapy or occupational therapy may be used to help the patient with recovering strength, everyday functioning, and healing. Current techniques involving immobility, physical therapy, or occupational therapy may not monitor or adequately assess range of motion or for pain before or after surgical intervention.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
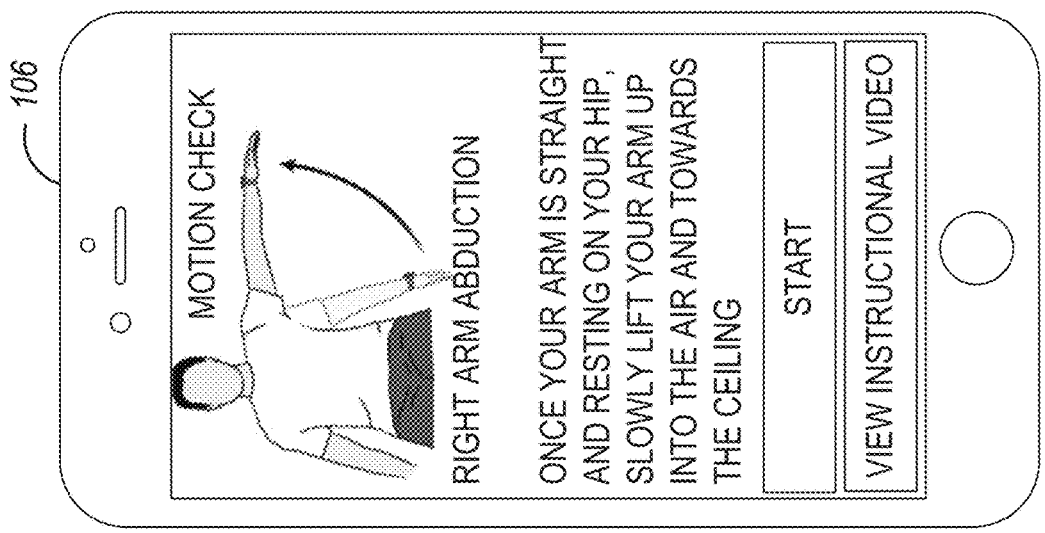
FIG. 1 illustrates user interfaces for directing a patient to perform a movement in accordance with at least one example of this disclosure.
Figure 1:
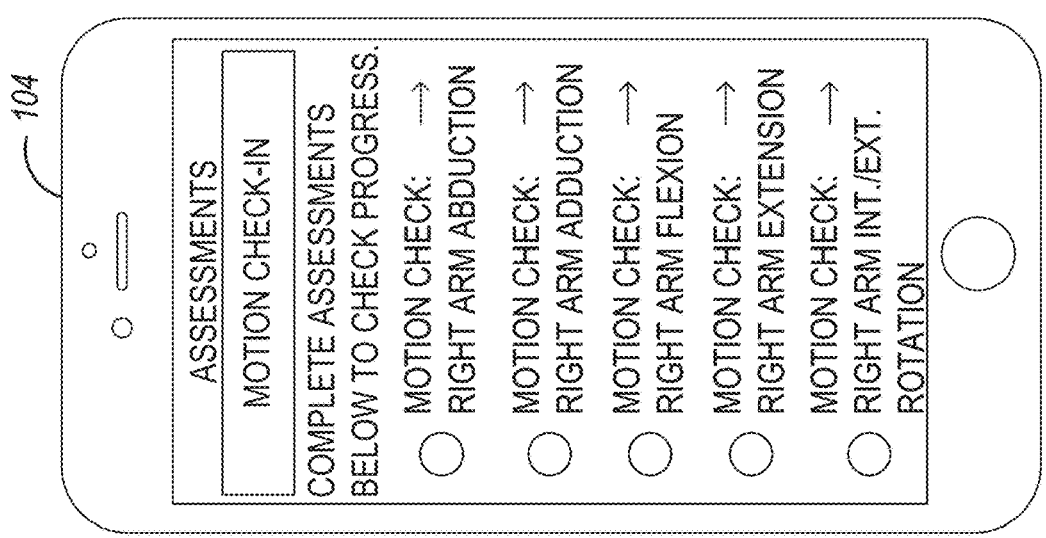
Figure 1:
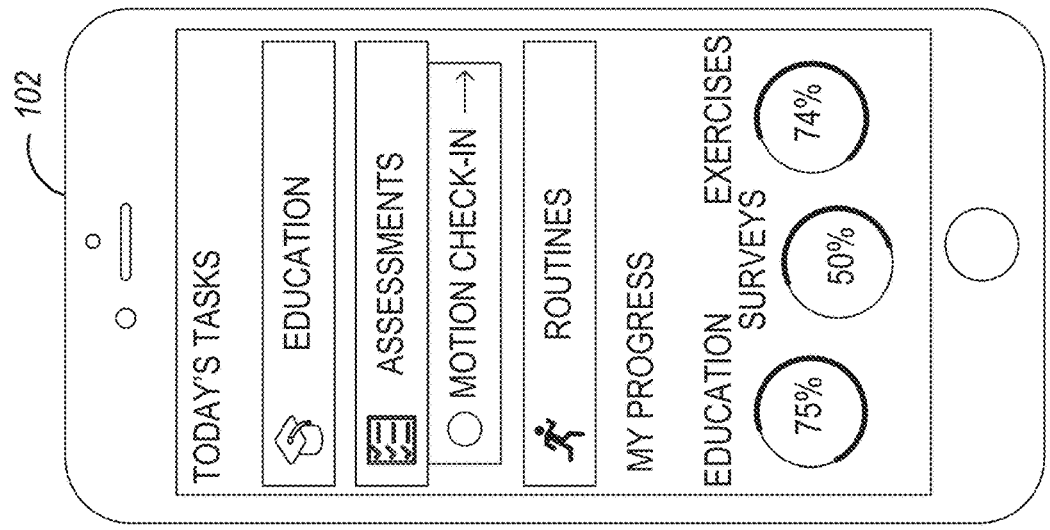

Systems and methods described herein may be used for evaluating a patient after completion of an orthopedic surgery on a portion of a body part of the patient in accordance with at least one example of this disclosure. The orthopedic surgery may include a joint repair, replacement, revision, or the like. The evaluation of a patient is an important post-surgical aspect of recovery. Proper adherence to exercises, accuracy in range of motion testing, and accuracy in other movements may normally be difficult to assess or maintain for a patient. However, the adherence or accuracy is necessary to ensure that the patient recovers. For example, improper exercise may exacerbate rather than improve movement functioning. Inaccuracies in range of motion or movement testing may cause incorrect diagnoses, incorrect milestones, or otherwise frustrate a patient or delay positive outcomes or goals. In some examples, the systems and methods described herein may be used for pre-operative assessment, benchmarking (e.g., during treatment or physical therapy recover, for example), or post-operatively.

Proper adherence to physical and occupational therapy post-surgery is critical to a patient's complete recovery of motion and strength. Patients are typically only able to attend in-person physical therapy session once or twice a week, but the regiment of exercises must be followed daily. Additionally, it is often difficult for patients to fully comply with exercise regiments on their own, as they are unable to assess whether they are performing the exercises correctly. The systems and methods described herein address these challenges by providing patients with a portable convenience system to track compliance and assess performance of the various exercises. For example, system and methods described herein may be used to accurately track compliance and progress in various movements of the affected joint or limb, or accurately track range of motion recovery. As discussed in greater detail below, a system may be calibrated to a particular user such that the particular user's movements are accurately tracked. In some examples, accuracy may be continuously monitored to ensure that a patient does not drift away from an accurate movement over time.

In an example, a calibration may be performed using a camera (e.g., a camera of a mobile device, such as a phone or tablet, a computer, or the like). The calibration may include determining a maximum limb length of a limb as a patient moves the limb. The maximum limb length, once identified, may be used to align the user (e.g., via visual, audio, haptic, or other feedback) for performing an exercise (e.g., a physical or an occupational therapy movement, a range of motion test, etc.).

Systems and methods described herein may be used to identify a movement plane for a limb of a user that is most orthogonal to a central line of sight of a camera. For example, a central line of sight of a camera may include a line extending out from the camera in a most central portion of a field of view (e.g., a line extending from a center point of a lens of the camera). The movement plane may be orthogonal (e.g., perpendicular or substantially perpendicular) to the line extending from the camera. The movement plane may not be entirely orthogonal. For example, the systems and methods described herein may determine a most orthogonal from among possible movement planes identified for a patient.

The patient may be instructed to move the limb along a plane parallel to the camera line (e.g., orthogonal to the movement plane). As the patient moves the limb, the camera may capture images of the limb. A processor (e.g., of a device also housing the camera, or of a separate device) may use the captured images to determine apparent limb lengths in each of or a set of the images. The apparent limb lengths may be compared, and a maximum limb length may be selected. The maximum limb length may be used to define the movement plane.

In some examples, a minimum for the maximum limb length may be used. For example, if the maximum limb length is too short, the systems and methods described herein may include providing instructions to the patient to attempt to calibrate again. In other examples, further instructions may be provided to the patient to aid in achieving a sufficient maximum limb length.

Instructions may be provided to the patient to aid in the calibration. A display screen may be used to display (e.g., on a user interface) directions to a patient to rotate a body part (e.g., limb) about an axis perpendicular to a line of sight of a camera. By rotating around this axis, the patient moves the limb in a plane substantially parallel to the line of sight of the camera. For example, considering the axis to be aligned in a central portion of the patient's body, the patient may rotate an arm fully extended outward by rotating at the hips or turning the feet or ankles.

In an example, the systems and methods described herein may be used to determine respective lengths of a body part or limb in images captured by the camera. The respective lengths may be determined based on comparing the body part in each of the series of images to a skeletal model. The skeletal model may be a joint and limb model, which may identify, in an image or series of images, a location of various joints and limbs. Using the determined respective lengths, a maximum length of the limb or body part may be identified.

In an example, an indication corresponding to the maximum length may be output. For example, a captured image corresponding to the maximum length may be displayed on a user interface. A tone or other audio may be played to indicate the maximum length. For example, audio may be varied according to how close the patient is to achieving the maximum length or audio may be played when the patient achieves the maximum length. Outputting the maximum length may include displaying an indication overlaid on live images (e.g., real-time captures by the camera), which may include instructions for achieving the maximum length. These instructions may include directions, such as move the limb closer to the camera or further away, or more generally information, such as move slowly, for example when the patient is close to achieving the maximum length. In an example, the indication may be removed from display when the body part is identified to be at a length shorter than the maximum length, such as by at least a threshold length.

After calibration is complete (e.g., a maximum length is identified), the display screen may display an exercise (e.g., for physical or occupational therapy, for a range of motion test, or for other goal-related movements) to be completed by the patient using the body part or limb while the body part or limb is at the maximum length. In this example, the camera may capture range of motion or other exercise-related data of the body part during the exercise. During or after the exercise, an indication related to the exercise or generally to recovery from the orthopedic surgery may be output (e.g., displayed). The indication may be output based on the captured range of motion data or the other exercise-related data.

A skeletal model may be used to track or identify body part, joint, or limb locations of a patient. Using the skeletal model, the patient may be tracked or have portions of the patient identified without use of a depth camera, without the use of depth sensors, without the use of a gait lab, without the use of markers (e.g., a preidentified visible indicator, such as a sticker or clothing, on a user), or the like. Movements or locations may be detected for the patient.

Tracking exercise movement or identifying a location of a patient may include tracking reps (e.g., for a physical therapy activity or training regimen), tracking time a position is held, monitoring for correct performance of an exercise or movement, or the like. The automatic tracking may allow a user to focus on the movement or technique performed without worrying about needing to keep a count, time, or movement in their head. The tracked movement, reps, or time may be used for a physical therapy session, such as for rehab or strength training. In an example, the tracked information is used for rehab after an orthopedic surgery, for example to monitor user progress, provide feedback to the user or a clinician, or the like.

A trained skeletal model may be used to process images of a user captured by a camera. The camera may be a camera of a mobile device (e.g., a cell phone), in an example. The camera may not be a depth camera or include any additional sensors beyond those of a digital camera.

The skeletal models described herein may be generated based on joints and change in joint angles. In an example, a skeletal model may be scaled to match a patient. In an example, a patient's movements may be captured, an exercise identified, and a portion of user anatomy tracked, (optionally in real-time) via a camera of a mobile device (e.g., a phone).

A progress update user interface may display a daily living task (e.g., putting on a t-shirt) that the patient has performed (e.g., determined at the suggestion of a user interface, or upon information supplied by the patient, or based on sensor data indicating a particular movement corresponding to putting on a t-shirt). The progress update interface may include a question about pain, which may be used by a clinician to monitor patient pain over time or with particular tasks. An example task may include reaching above a specified height, such as for washing hair, putting on a t-shirt, brushing hair reaching above head to a shelf, etc. Another example task may include detecting extension and internal rotation, such as putting a jacket on, tucking in a shirt, putting a bra on, etc.

FIG. 1 illustrates user interfaces for directing a patient to perform a movement in accordance with at least one example of this disclosure. The user interfaces (e.g., 102, 104, and 106) shown in FIG. 1 may be implemented on a single device (e.g., sequentially displayed) or on different devices. The user interfaces of FIG. 1 may include selectable indications, information (e.g., instructions, education, etc.), video, or the like. In FIG. 1, example user interfaces are shown with example components, but it is understood that components may be changed (e.g., rearranged, differ in style or content, etc.), and still work with the systems and methods described herein.

Specifically, user interface 102 illustrates various selectable indications including ones for education, assessments, and routines, as well as information related to progress (e.g., for monitoring patient recovery from an orthopedic procedure). In an example, the patient may select the "motion check-in" indication under the "assessments" group. After selection, user interface 104 may be displayed. User interface 104 includes one or more assessments corresponding to the "motion check-in" task. The specific motion check-in shown in user interface 104 includes right arm assessments, such as a right arm abduction assessment. After selection of the right arm abduction assessment on user interface 104, user interface 106 may be displayed. User interface 106 includes instructions (e.g., "Once your arm is straight and resting on your hip, slowly lift your arm up into the air and towards the ceiling") for completion of the assessment exercise. User interface 106 includes selectable indications to start the exercise (e.g., which may include turning on a camera automatically to track movement of the patient) or view an instructional video for further directions.

In an example, the exercise progression shown in FIG. 1 may be performed after calibration. In another example, calibration may interrupt the exercise progression (e.g., after selection of "Start" on user interface 106, after selection of "motion check-in" on user interface 102, etc.). Calibration as described herein may be used to ensure accuracy and precision of tracking during exercises (e.g., the arm abduction assessment exercise).

The user interfaces 102, 104, and 106 may be displayed on a mobile device (e.g., cell phone or tablet). A camera of the mobile device may be used to capture movement of the patient (e.g., when the patient attempts the exercise) as well as for calibration. Using the calibration systems and techniques described herein, the mobile device may be used to accurately and precisely capture and provide feedback to the patient performing the exercise.

Figure 2:
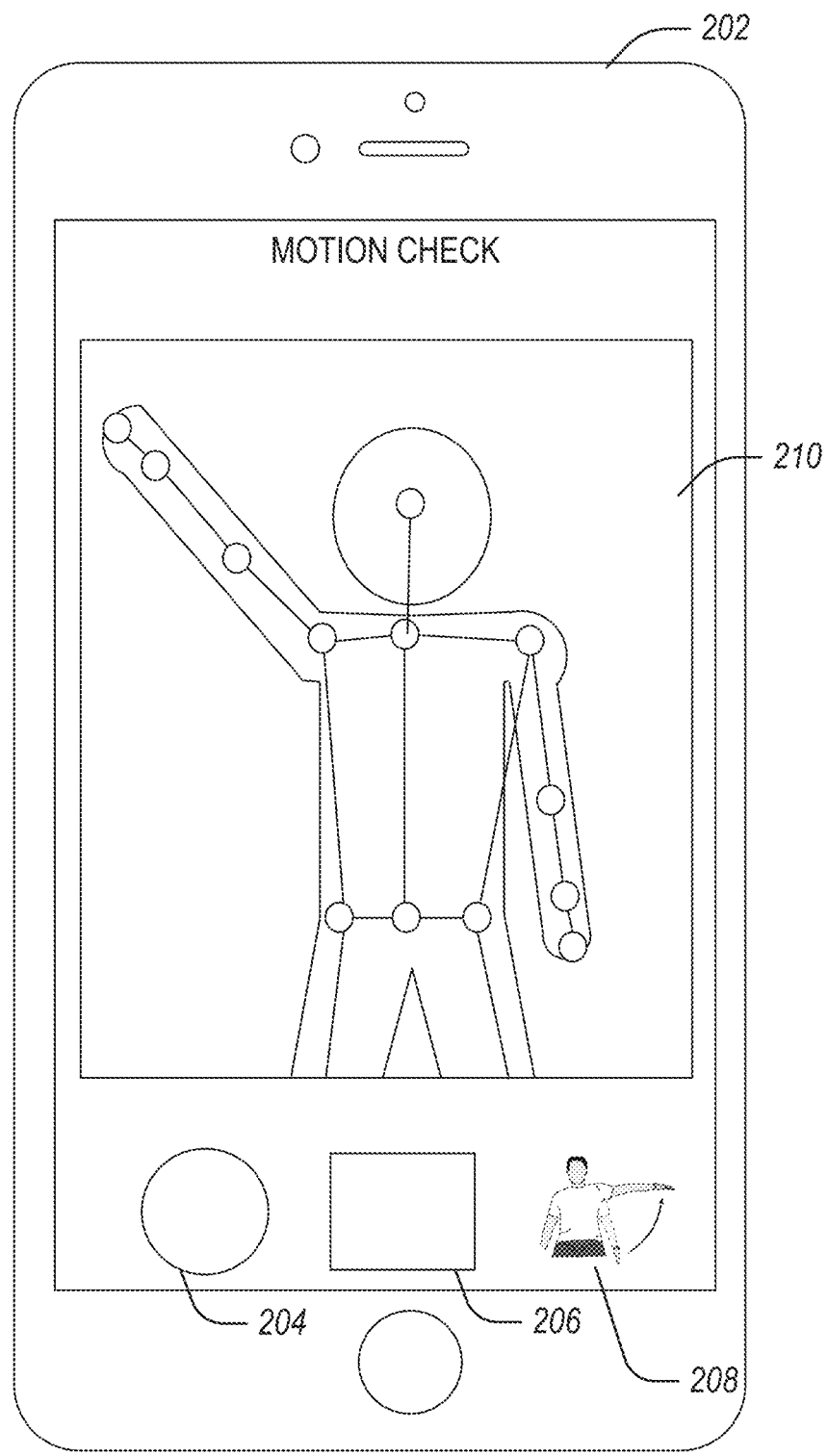
FIG. 2 illustrates a user interface for checking planar and angular attributes of a user movement or pose in accordance with at least one example of this disclosure.

FIG. 2 illustrates a user interface for checking planar and angular attributes of a user movement or pose in accordance with at least one example of this disclosure. The ability to validate certain planar and angular movements improves the system ability to assess a patient's compliance and process towards full recovery. FIG. 2 illustrates a user interface 202 displaying an image captured of a patient performing an exercise (e.g., the right arm abduction motion assessment exercise). Selectable indications 204 and 206 may be used to start (204) and stop (206) video capture or playback. An indication 208 of the current exercise is also shown. The user interface 202 includes an image or video display portion 210 to playback or display a live image of the patient attempting the exercise. The display portion 210 includes skeletal tracking information overlaid on the patient, but this information may be omitted in some examples.

Figure 3:
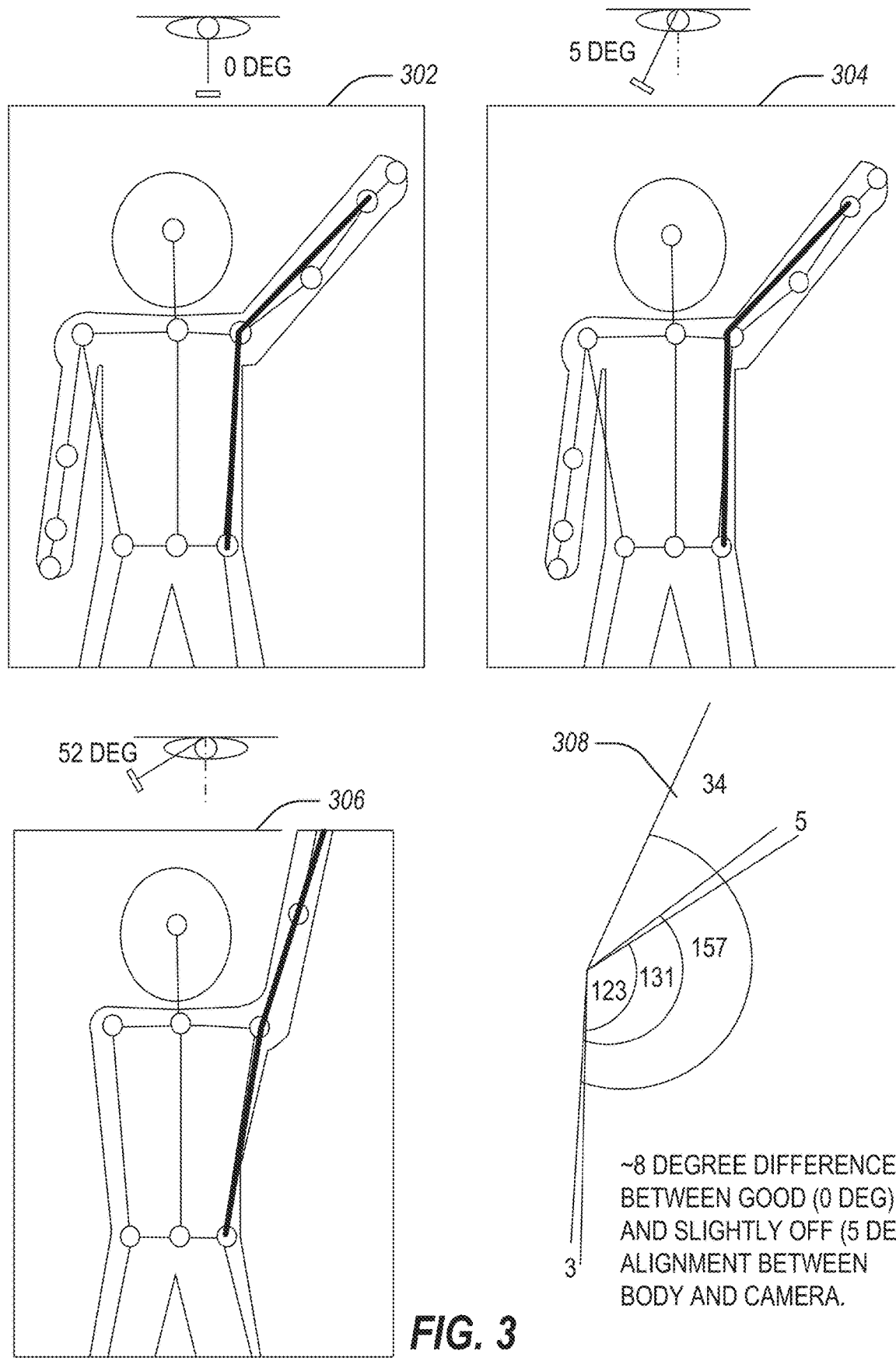
FIG. 3 illustrates various alignment examples for planar accuracy based on camera alignment in accordance with at least one example of this disclosure.

FIG. 3 illustrates various alignment examples for planar accuracy based on camera alignment in accordance with at least one example of this disclosure. The alignment examples illustrate the issues that may occur with using a camera to track rotation angles of limbs (e.g., for range of motion or exercises) without the calibration techniques described herein.

The examples (302-306) illustrate a user in various alignments, including an alignment corresponding to a maximum limb length (in this case an arm) in example 302, and two alignments corresponding to limb lengths less than the maximum in examples 304 and 306. Examples 302 and 304 show the limb at substantially a same angle relative to the user's body, but with different alignments with respect to a camera that captured images of examples 302 and 304. In example 304, the misalignment with respect to the camera causes a five-degree error to be introduced. Without the calibration techniques described herein, a user may accidentally align themselves as in example 304, causing the collected data to be incorrect. These issues may be exacerbated by larger limbs, further distances from the camera to the user, or as time goes on while the user performs an exercise or range of motion test.

Example 304 is shown with a five-degree offset in the camera alignment (e.g., the user in example 304 is offset five degrees from the maximum length plane the user is aligned with in example 302). However, this five-degree offset, when calculating the user's limb angle with respect to the user's body causes an eight-degree error, as seen in diagram 308. For example, the user's limb appears to be eight degrees further from the user's torso (e.g., the substantially vertical line in example 304) than the correctly calculated angle in example 302. In the examples shown, the limb to torso angle in example 304 is 131 degrees, while the limb to torso angle in example 302 is 123 degrees. The user in both examples 302 and 304 has an equal limb to torso angle, so the 131 to 123 degree difference is the error.

By performing the calibration techniques described herein, the user may obtain the more accurate measurements corresponding to example 302, rather than the errors present in examples 304 and 306. Example 306 illustrates a more extreme example where a 34 degree offset in camera to user plane corresponds with a 34 degree error in limb to torso angle determination, as shown in diagram 308.

Figure 4:
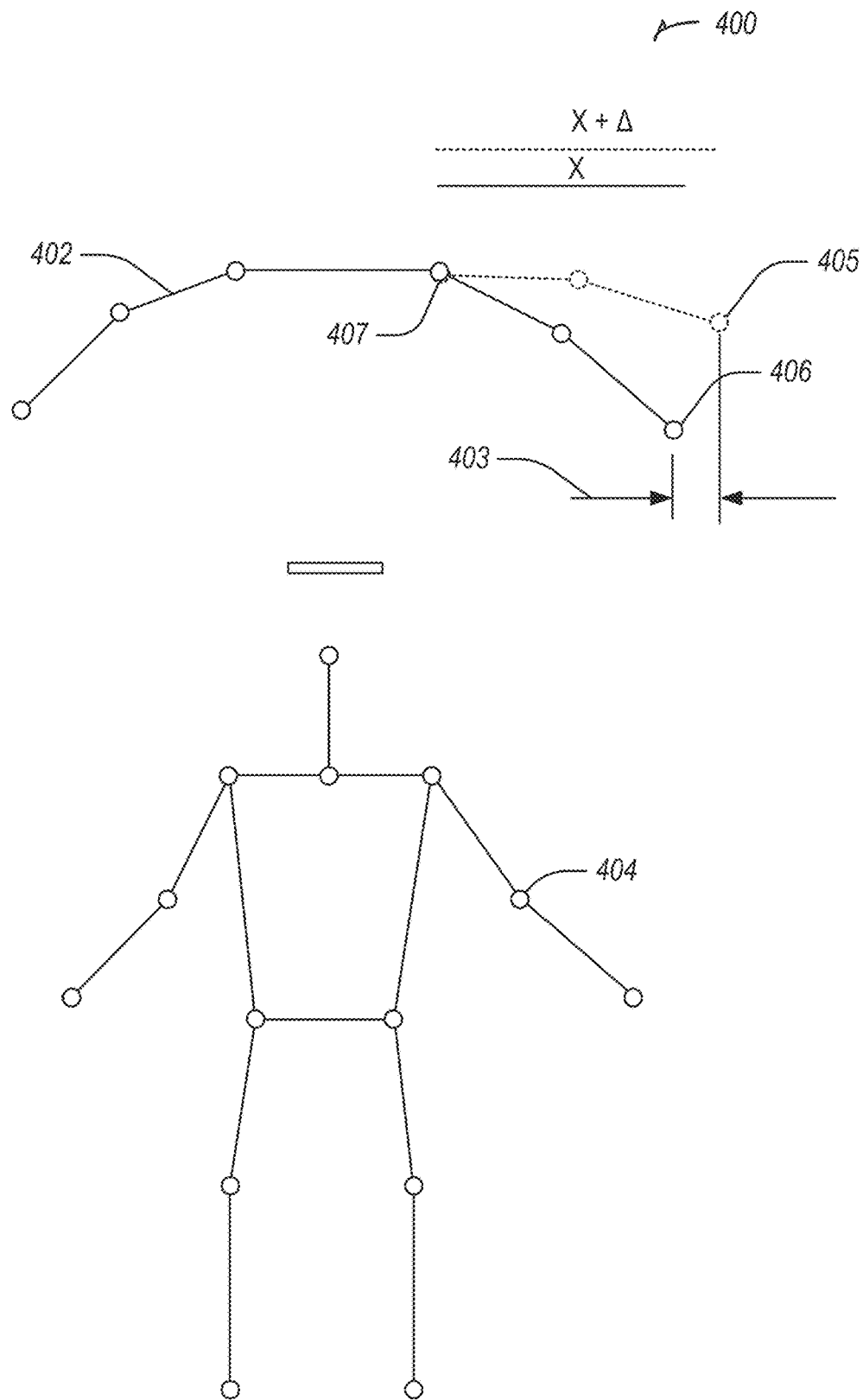
FIG. 4 illustrates a diagram showing a limb length alignment system in accordance with at least one example of this disclosure.

FIG. 4 illustrates a diagram 400 showing a limb length alignment system in accordance with at least one example of this disclosure. The diagram includes an overhead view 402 of a skeletal model of a patient and a front facing view 404 of the skeletal model of the patient. The overhead view 402 shows the patient in two different alignments with a first perceived distance (X+delta) at endpoint 405 and a second perceived distance (X) at endpoint 406. The delta 403 is the difference between the first and second perceived distances.

The first perceived distance may be identified from a captured image of the patient as being a larger distance than the second perceived distance. Because the first perceived distance is greater than the second, the alignment when the patient has a limb at endpoint 405 may be saved as a maximum length alignment (e.g., in this limited example with two end point alignments, for example; in other examples more endpoint alignments may be used).

The delta represents a difference in limb length due to out-of-plane alignment. Before collecting movement data related to an exercise or range of motion evaluation, the patient may rotate in and out of the maximum plane (which may not be known to the patient) to find a maximum limb length, which occurs when alignment is perpendicular to the camera.

During movement (e.g., during an exercise or range of motion evaluation), limb length may be tracked. Deviations from the previously identified maximum limb length correspond to an amount out of plane the motion is, and may be identified or corrected (e.g., with an alert, a user interface indication, using a distance correction technique, or the like).

A system may trigger an alert when the patient moves too far out of plane (e.g., when limb length is identified as being too short). In an example, the alert tells the patient to re-align to camera. In another example, the alert flags reported data as being too out of plane (e.g., the data is to be disregarded).

The patient may be instructed to rotate a limb (e.g., an arm) in and out of a maximum plane (e.g., towards and away from a camera), such as by rotating their body to find a maximum limb length. The maximum limb length may be used to align the user to the camera.

The skeletal representations in the overhead view 402 and the front view 404 may be retrieved from a library of skeletal data. The skeletal data may be used to determine the limb length. For example, a distance from a first skeletal point (e.g., point 407) to the endpoints 405 and 406 may be determined, and a maximum distance may be used as the maximum length of the limb represented by links from point 407 to 405 or 406. In an example, endpoints 405 and 406 are the same portion of a limb, but in different orientations. In an example, point 407 remains constant. In other examples, point 407 moves, and other points are used to adjust for the movement of point 407 to maintain a standard distance measurement.

The maximum length may not correspond to a maximum possible length, but may be a maximum length from among lengths measured. In some examples, a tolerance range for the maximum length may be used (e.g., a minimum length for the maximum length may be required for the maximum length to be considered valid, such as 1 degree, 3 degrees, 5 degrees, etc.).

The measured limb length may not necessarily correspond with absolute limb size, but instead may correspond with an amount of an image that is occupied by the limb.

In some examples, alerts during calibration may be issued based on identifying that the limb being measured is not in view of the camera, identifying that the limb is being moved in a circle instead of in a plane, or other deviations from planar movement for example, or the like. In an example, during an exercise or range of motion test, an alert may be provided that identifies when the limb is out of alignment, but the patient otherwise appears to be performing the exercise correctly.

In some examples, more than one camera may be used. The use of more than one camera may be used to increase accuracy of calibration or capture of exercise movements or range of motion movements.

Figure 5:
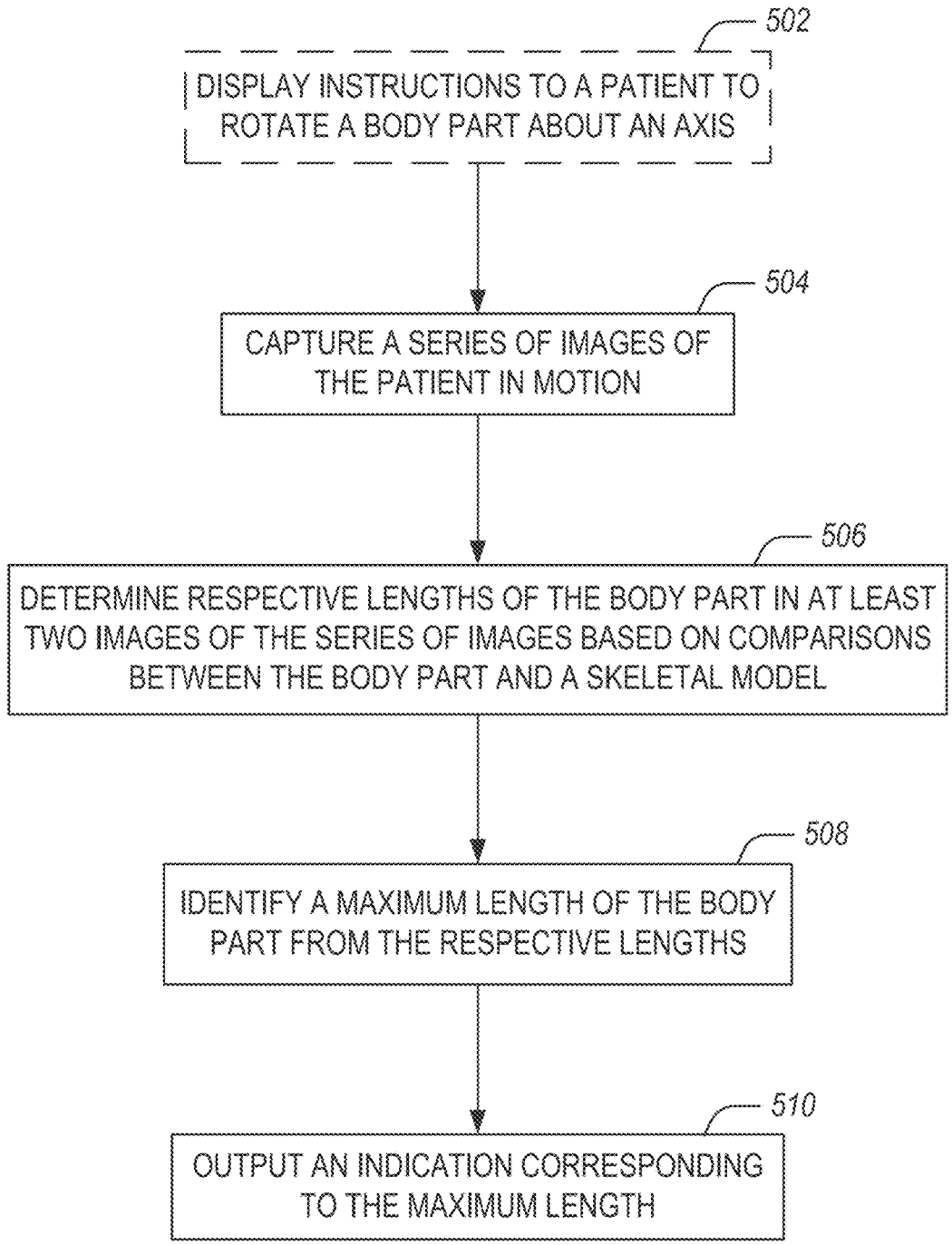
FIG. 5 illustrates a flowchart showing a technique for evaluating a patient after completion of an orthopedic surgery on a portion of a body part of the patient in accordance with at least one example of this disclosure.

FIG. 5 illustrates a flowchart showing a technique 500 for evaluating a patient after completion of an orthopedic surgery on a portion of a body part of the patient in accordance with at least one example of this disclosure. A body part as used herein may refer to an appendage, a set portion of a body, an area of a body, etc. For example, a body part may include an arm plus a shoulder, such as to include shoulder joint when shoulder joint was a surgical intervention. In another example, a body part may include a leg, such as when a knee was the surgical intervention. In yet another example, a body part may include a leg with a hip joint, with optional aspects of the pelvis region included. In an example, a body part includes a moveable portion of the body that is evaluable for changes in perceived length according to examples disclosed herein. A body part may include a finger, a head and neck, a leg from the knee down (e.g., from the knee joint distally), a leg from a hip joint distally, a toe, a foot from an ankle joint distally, an arm from a wrist, elbow, or shoulder joint distally, etc.

A length as discussed herein may include a distance from one end of a body part to an opposite end of the body part. For example, from a proximate end of the body part to a distal end of the body part. This may include a measurement from a joint to tip (e.g., elbow joint to tip of finger) or joint to joint (e.g., shoulder joint to wrist joint), or the like.

The technique 500 includes an optional operation 502 to display instructions to a patient to rotate a body part about an axis. The axis may include an axis perpendicular to a line of sight of a camera. Optional operation 502 may include displaying the instructions on a display screen (e.g., on a user interface) of a user device, which may include the camera. The user device may be a mobile phone, tablet, computer, etc.

The technique 500 includes an operation 504 to capture a series of images of the patient in motion. The series of images may be captured by the camera. In an example, the series of images include at least three images, including at least two images identifying the body part at a length shorter than the maximum length. For example, one image (or a first set of images) may show the body part at shorter lengths due to being further away from the camera than a plane corresponding to the maximum length. Another image (or a second set of images) may show the body part at shorter lengths due to being closer to the camera than the plane corresponding to the maximum length. While the maximum length may not correspond exactly to a maximum possible length, by having the patient move from behind to in front (or vice versa), and optionally perform that movement multiple times, a likelihood of finding the maximum possible length (at least within a tolerance range) is high. Some images may be captured interspersed with the series of images, which are not used to determine a length of the body part (e.g., when the body part is not visible, when the length cannot be resolved, when the image is blurry, when the camera moves, etc.).

The technique 500 includes an operation 506 to determine respective lengths of the body part in at least two images of the series of images based on comparisons between the body part and a skeletal model. Operation 506 may be performed using a processor of the user device. In an example, operation 506 includes determining respective lengths for each image in the series of images. Operation 506 may include using skeletal tracking of the body part as well as a portion of the patient other than the body part. For example, when the body part is an arm, the tracking may include resolving the torso or the shoulder of the patient.

The technique 500 includes an operation 508 to identify a maximum length of the body part from the respective lengths. The maximum length may correspond to a plane perpendicular to a line of sight of the camera, the plane intersecting the body part.

The technique 500 includes an operation 510 to output an indication corresponding to the maximum length. Operation 510 may include displaying, on a user interface of the display screen of the user device. Operation 510 may include displaying the indication while the camera continues to capture images. For example, the indication may be displayed only when the body part is at the maximum length. In an example, instructions may be provided to move the body part in a particular direction (e.g., closer or further away from the camera) to achieve the maximum length. The indication may be overlaid on a live image of the patient, for example when the body part is at the maximum length. The indication may be removed from display (or changed, for example to instructions) when the body part is identified to be at a length shorter than the maximum length, for example by at least a threshold length.

The technique 500 may include an operation to display an exercise to be completed by the patient using the body part while the body part is at the maximum length, for example on a user interface. During the exercise, the technique 500 may include capturing range of motion data of the body part using the camera. The range of motion data may be used to output at least one indication related to recovery from the orthopedic surgery. The output indication may be sent to a clinician or member of a care team (e.g., a physical therapist, a surgeon, family member, etc., such as via an email or update to a profile of the patient) or output to the patient (e.g., displayed on a patient device, such as the user device used to complete the exercise).

Figure 6:
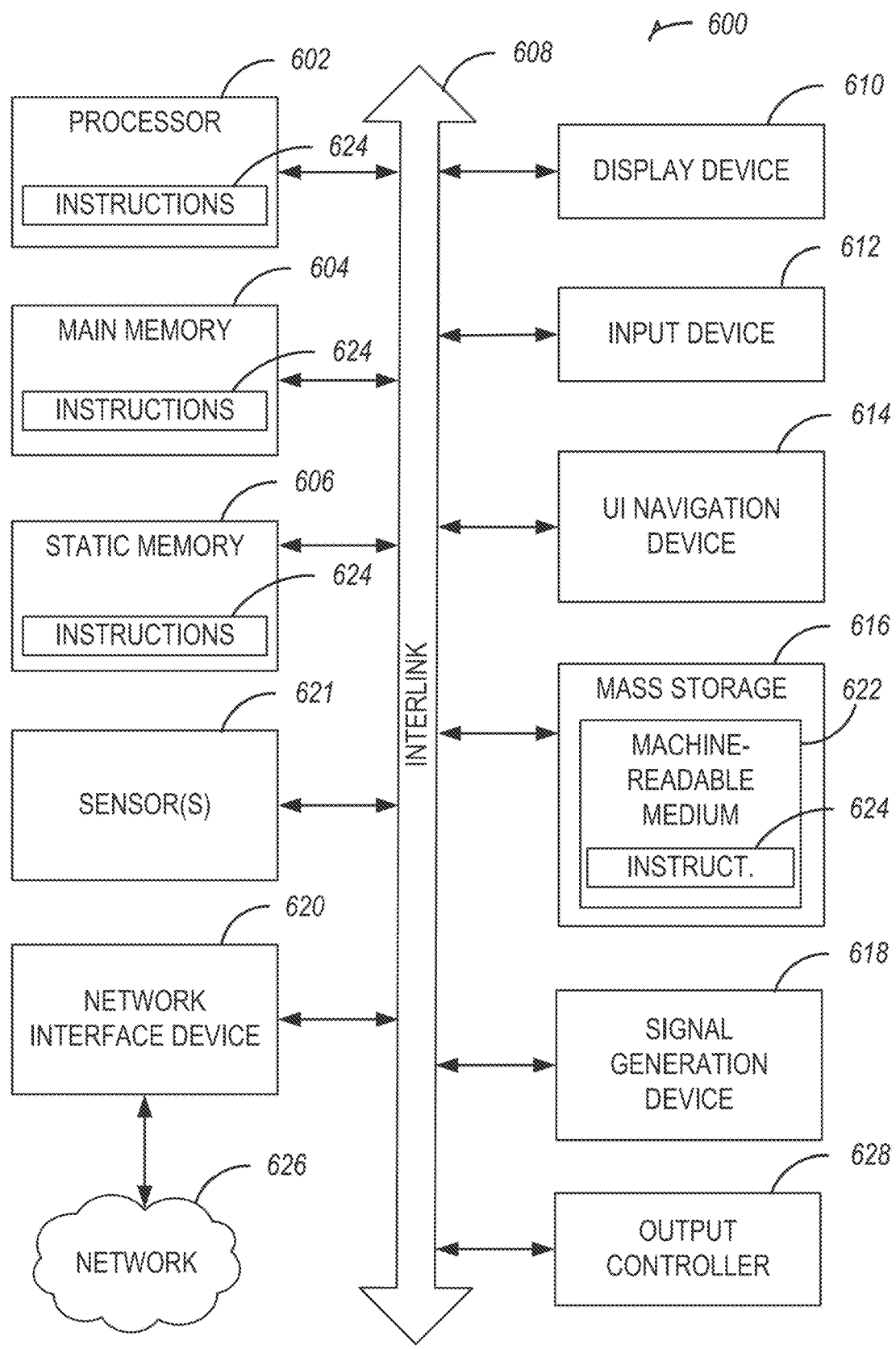
FIG. 6 illustrates a block diagram of an example machine upon which any one or more of the techniques discussed herein may perform in accordance with at least one example of this disclosure.

FIG. 6 illustrates a block diagram of an example machine 600 upon which any one or more of the techniques discussed herein may perform in accordance with some embodiments. In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610, an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine readable media.

While the machine readable medium 622 is illustrated as a single medium, the term "machine readable medium" may include a single medium or multiple media (e.g., a centralized or distributed database, and/or associated caches and servers) configured to store the one or more instructions 624. The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine-readable medium examples may include solid-state memories, and optical and magnetic media.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Figure 7A:
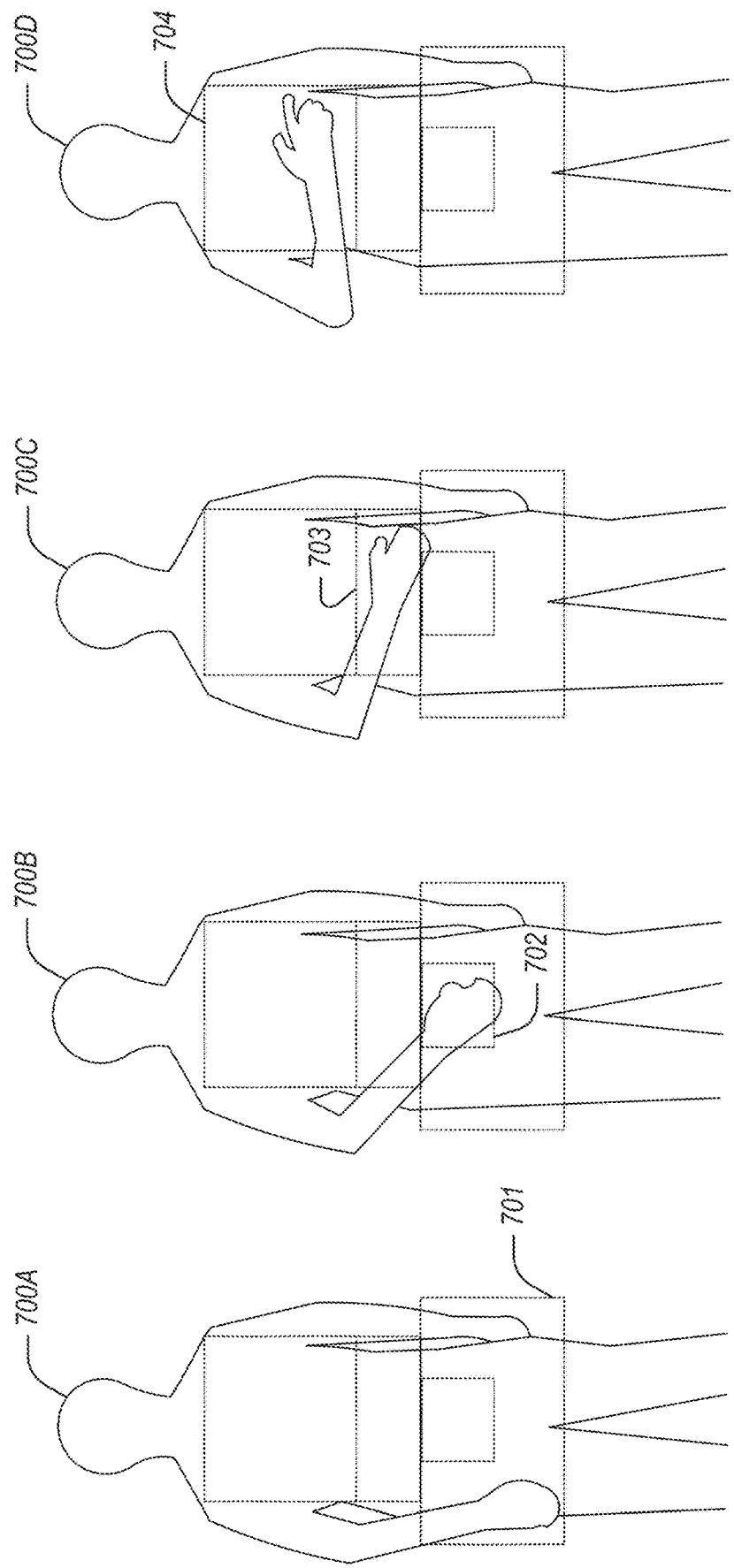
FIGS. 7A-7B illustrate an example framework for back internal rotation scoring in accordance with at least one example of this disclosure.
Figure 7B:
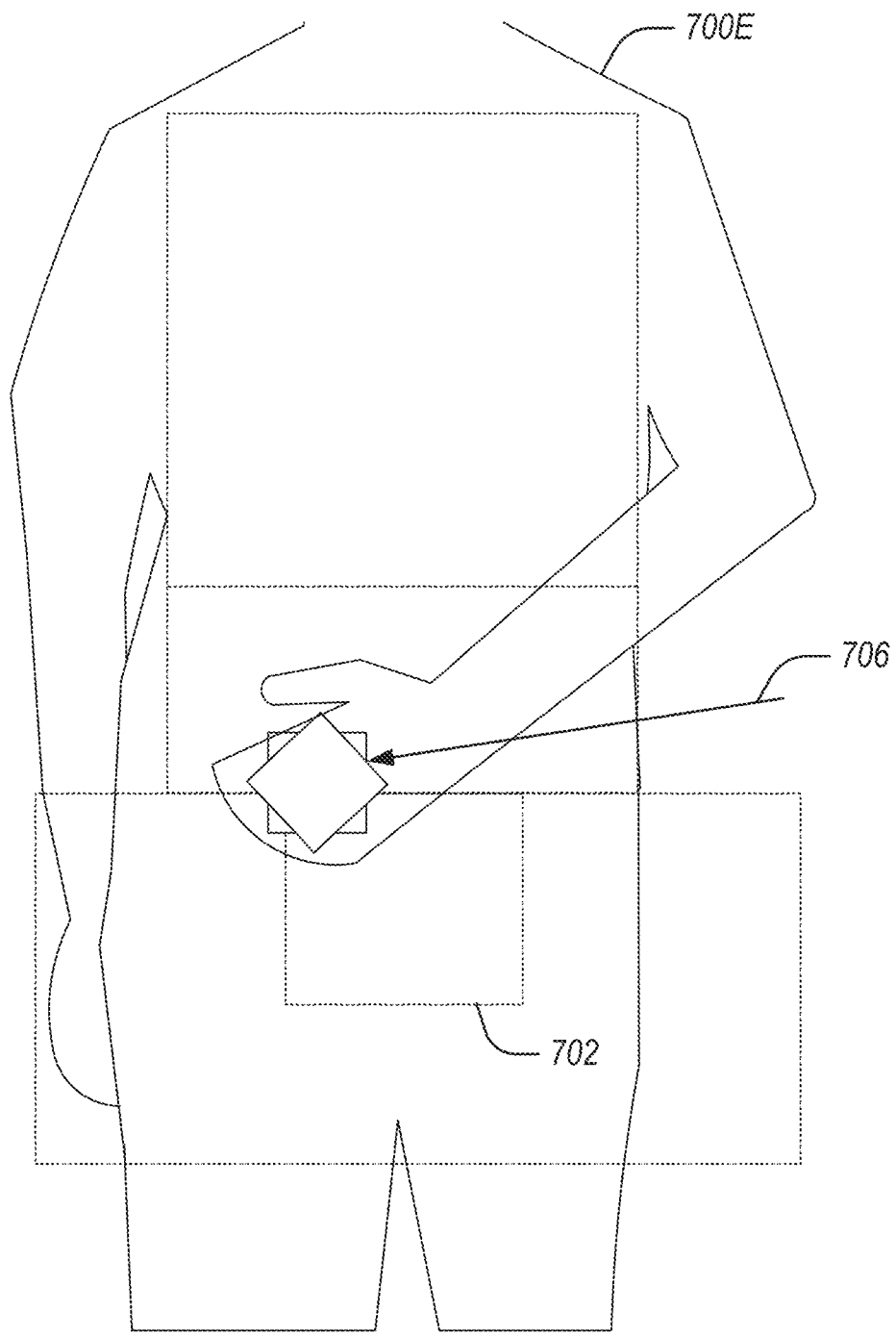

FIGS. 7A-7B illustrate an example framework for back internal rotation scoring in accordance with at least one example of this disclosure. FIG. 7A shows four example hand positions of a patient, with each hand position corresponding to a different back internal rotation score. The patient is shown facing away from the viewer, with a left hand behind the patient's back in FIG. 7A, and a right hand behind the patient's back in FIG. 7B.

In FIG. 7A, patient 700A has the left hand in a first box 701 corresponding to a score of one. Patient 700B has the left hand in a second box 702, corresponding to a score of two. Patient 700C has the left hand in a third box 703 (in some examples, box 703 is identified by a line creating two boxes from a larger box, which includes box 704) corresponding to a score of three. Patient 700D has the left hand in a fourth box 704 corresponding to a score of four. These scores represent a range of motion of the patient.

The back internal rotation assessment may use a scoring system of four quadrants, as opposed to a broad range of angle measurements used in some traditional evaluations. Instead of using angle measurements to score a patient's range of motion, the back internal rotation assessment uses a quadrant score system, for example having a range of one through four. The quadrants used in this scoring system may differ (e.g., not be equal in area).

The scoring quadrants may be described according to patient anatomy. For example, natural variations occur in body types and there may be limitations in body landmark detection. The areas described may be approximate in practice. In an example, a patient achieves a quadrant one score by reaching any location from the starting position to the back of the patient's thigh on the assessed side (box 701). A patient achieves a quadrant two score by reaching to the patient's sacrum with the assessed limb's hand (box 702). A patient receives a quadrant three score by reaching to the area above the patient's sacrum and below the waist (box 703). A patient receives a quadrant four score by reaching the area on the upper back above the waist (box 704).

Some examples for the tracked joints for the left and right back internal rotation assessments are listed below. Instead of angle measurements, the x and y coordinates of each joint may be used for tracking and scoring. The non-assessed side may be referred to as the resting side.

The scoring box dimensions may be derived from a patient's joint positions. The resting side joints may be used to anchor the scoring boxes, as their positions may be more reliably static when compared to those on the assessed side.

The back box 704 may have a width having a distance of resting shoulder to assessed shoulder, a height of 80% of distance of resting shoulder to resting hip, an x-position that tracks x-position of resting shoulder, and a y-position that tracks y-position of resting shoulder. The back box divider 703 may include a width of 100% width of the back box 704, an x-position centered horizontally relative to the back box 704, and a y-position of 70% of the distance of resting shoulder to the back box 704 bottom border. The hips box 702 may include a width of 150% width of the back box 704, an height of 90% of the width of the back box 704, an x-position that is centered horizontally relative to the back box 704, and a y-position that shares its top border with the back box 704 bottom border. The sacrum box 701 may include a width of 50% of the width of the back box 704, a height of 50% of the height of the back box 704, an x-position centered horizontally relative to the back box 704, and a y-position that shares its top border with the back box 704 bottom border.

FIG. 7B illustrates a virtual interaction object 706 representing a transition from one box to another of the patient's hand. In some examples, to distinguish among the possible scores for a hand location, an additional object may be used. The object 706 may be used for quadrant one and two scoring. The object 706 may include a hand collider. The hand collider may be rendered as boxes (e.g., with one rotated 45 degrees) as shown in FIG. 7B. The object 706 may be used to help to determine when a patient's hand reaches, or collides with the quadrant two scoring box (e.g., box 702). The object 706 may be used to account for potential undercounting or missed scores in quadrant two. The object 706 may counteract the issues of undercounting due to the small size of the box 702, and the potential short amount of time that the hand point is detectable in the box 702 while in motion.

The object 706 may be used to define a larger detectable area around the user's assessed side hand. Although the box 702 size remains the same, the object 706 may help to increase the time that the hand is detectably inside of the box 702. In some examples, the object 706 may include a first hand collider with a width of 20% of the back box 704, a height of 20% of the width of the back box 704, an x-position that tracks the x-position of the assessed hand, and a y-position that tracks the y-position of the assessed hand. The object 706 may include a second hand collider with the same properties of the first hand collider (e.g., rotated 45 degrees).

Other versions of the object 706 may include different polygons or combinations of polygons. For example, low-poly shapes may be used to define more computationally expensive areas for real-time collision. Drawing from this real-time collision method, two rectangular shapes may be used to define an area surrounding the tracked hand point with a radius that approximated the width of the hand for the back internal rotation assessment.

Each of the following non-limiting examples may stand on its own, or may be combined in various permutations or combinations with one or more of the other examples.

Example 1 is a mobile device for evaluating a patient after completion of an orthopedic surgery on a portion of a body part of the patient, the mobile device comprising: a display screen configured to display directions to a patient to rotate the body part about an axis perpendicular to a line of sight of a camera; a camera configured to capture a series of images of the patient in motion; processing circuitry; and memory including instructions, which when executed, cause the processing circuitry to: determine respective lengths of the body part in each of the series of images based on comparing the body part in each of the series of images to a skeletal model; identify a maximum length of the body part from the respective lengths; and output an indication corresponding to the maximum length.

In Example 2, the subject matter of Example 1 includes, wherein the maximum length corresponds to a plane perpendicular to a line of sight of the camera, the plane intersecting the body part.

In Example 3, the subject matter of Examples 1-2 includes, wherein the series of images include at least three images, including at least two images identifying the body part at a length shorter than the maximum length.

In Example 4, the subject matter of Examples 1-3 includes, wherein the camera is further configured to capture additional images interspersed with the series of images, the additional images not used to determine a length of the body part.

In Example 5, the subject matter of Examples 1-4 includes, wherein to determine the respective lengths of the body part, the instructions further cause the processing circuitry to use skeletal tracking of a portion of the patient other than the body part.

In Example 6, the subject matter of Examples 1-5 includes, wherein the display screen is further configured to present the indication while the camera continues to capture images.

In Example 7, the subject matter of Examples 1-6 includes, wherein the display screen is further configured to present the indication by overlaying the indication on a live image of the patient when the body part is at the maximum length.

In Example 8, the subject matter of Examples 1-7 includes, wherein the display screen is further configured to remove the indication from display when the body part is identified to be at a length shorter than the maximum length by at least a threshold length.

In Example 9, the subject matter of Examples 1-8 includes, wherein the display screen is further configured to display an exercise to be completed by the patient using the body part while the body part is at the maximum length.

In Example 10, the subject matter of Example 9 includes, wherein the camera is further configured to capture range of motion data of the body part during the exercise.

In Example 11, the subject matter of Example 10 includes, wherein the instructions further cause the processing circuitry to output, based on the captured range of motion data, at least one indication related to recovery from the orthopedic surgery.

Example 12 is a method for evaluating a patient after completion of an orthopedic surgery on a portion of a body part of the patient, the method comprising: displaying, on a user interface of a device, instructions to a patient to rotate the body part about an axis perpendicular to a line of sight of a camera; capturing, using a camera of the device, a series of images of the patient in motion; determining, using a processor of the device, respective lengths of the body part in each of the series of images based on comparing the body part in each of the series of images to a skeletal model; identifying a maximum length of the body part from the respective lengths; and displaying, on the user interface, an indication corresponding to the maximum length.

In Example 13, the subject matter of Example 12 includes, wherein the maximum length corresponds to a plane perpendicular to a line of sight of the camera, the plane intersecting the body part.

In Example 14, the subject matter of Examples 12-13 includes, wherein the series of images include at least three images, including at least two images identifying the body part at a length shorter than the maximum length.

In Example 15, the subject matter of Examples 12-14 includes, capturing additional images interspersed with the series of images, the additional images not used to determine a length of the body part.

In Example 16, the subject matter of Examples 12-15 includes, wherein determining the respective lengths of the body part includes using skeletal tracking of a portion of the patient other than the body part.

In Example 17, the subject matter of Examples 12-16 includes, wherein displaying the indication includes displaying the indication while the camera continues to capture images.

In Example 18, the subject matter of Examples 12-17 includes, wherein displaying the indication includes overlaying the indication on a live image of the patient when the body part is at the maximum length.

In Example 19, the subject matter of Examples 12-18 includes, removing the indication from display when the body part is identified to be at a length shorter than the maximum length by at least a threshold length.

In Example 20, the subject matter of Examples 12-19 includes, displaying, on the user interface an exercise to be completed by the patient using the body part while the body part is at the maximum length.

In Example 21, the subject matter of Example 20 includes, capturing range of motion data of the body part using the camera during the exercise.

In Example 22, the subject matter of Example 21 includes, based on the captured range of motion data, outputting at least one indication related to recovery from the orthopedic surgery.

In Example 23, the subject matter of Examples 12-22 includes, displaying, on the user interface, instructions to the patient to correct an alignment of the body part to obtain the maximum length.

Example 24 is at least one machine-readable medium including instructions that, when executed by processing circuitry, cause the processing circuitry to perform operations to implement of any of Examples 1-23.

Example 25 is an apparatus comprising means to implement of any of Examples 1-23.

Example 26 is a system to implement of any of Examples 1-23.

Example 27 is a method to implement of any of Examples 1-23.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A mobile device for evaluating a patient after completion of an orthopedic surgery on a portion of a body part of the patient, the mobile device comprising: a display screen configured to display directions to a patient to rotate the body part about an axis perpendicular to a line of sight of a camera; a camera configured to capture a series of images of the patient in motion; processing circuitry; and memory including instructions, which when executed, cause the processing circuitry to: determine respective lengths of the body part in each of the series of images based on comparing the body part in each of the series of images to a skeletal model; identify a maximum length of the body part from the respective lengths; and output an indication corresponding to the maximum length.

2. The device of claim 1, wherein the maximum length corresponds to a plane perpendicular to a line of sight of the camera, the plane intersecting the body part.

3. The device of claim 1, wherein the series of images include at least three images, including at least two images identifying the body part at a length shorter than the maximum length.

4. The device of claim 1, wherein the camera is further configured to capture additional images interspersed with the series of images, the additional images not used to determine a length of the body part.

5. The device of claim 1, wherein to determine the respective lengths of the body part, the instructions further cause the processing circuitry to use skeletal tracking of a portion of the patient other than the body part.

6. The device of claim 1, wherein the display screen is further configured to present the indication while the camera continues to capture images.

7. The device of claim 1, wherein the display screen is further configured to present the indication by overlaying the indication on a live image of the patient when the body part is at the maximum length.

8. The device of claim 1, wherein the display screen is further configured to remove the indication from display when the body part is identified to be at a length shorter than the maximum length by at least a threshold length.

9. The device of claim 1, wherein the display screen is further configured to display an exercise to be completed by the patient using the body part while the body part is at the maximum length.

10. The device of claim 9, wherein the camera is further configured to capture range of motion data of the body part during the exercise.

11. The device of claim 10, wherein the instructions further cause the processing circuitry to output, based on the captured range of motion data, at least one indication related to recovery from the orthopedic surgery.

12. A method for evaluating a patient after completion of an orthopedic surgery on a portion of a body part of the patient, the method comprising:
displaying, on a user interface of a device, instructions to a patient to rotate the body part about an axis perpendicular to a line of sight of a camera;
capturing, using a camera of the device, a series of images of the patient in motion;
determining, using a processor of the device, respective lengths of the body part in each of the series of images based on comparing the body part in each of the series of images to a skeletal model;

identifying a maximum length of the body part from the respective lengths; and displaying, on the user interface, an indication corresponding to the maximum length.

13. The method of claim 12, wherein the maximum length corresponds to a plane perpendicular to a line of sight of the camera, the plane intersecting the body part.

14. The method of claim 12, wherein the series of images include at least three images, including at least two images identifying the body part at a length shorter than the maximum length.

15. The method of claim 12, further comprising capturing additional images interspersed with the series of images, the additional images not used to determine a length of the body part.

16. The method of claim 12, wherein determining the respective lengths of the body part includes using skeletal tracking of a portion of the patient other than the body part.

17. The method of claim 12, wherein displaying the indication includes displaying the indication while the camera continues to capture images.

18. The method of claim 12, wherein displaying the indication includes overlaying the indication on a live image of the patient when the body part is at the maximum length.

19. The method of claim 12, further comprising removing the indication from display when the body part is identified to be at a length shorter than the maximum length by at least a threshold length.

20. The method of claim 12, further comprising displaying, on the user interface, instructions to the patient to correct an alignment of the body part to obtain the maximum length.

\* \* \* \* \*